United States Patent [19]
Errico et al.

[11] Patent Number: 5,904,719
[45] Date of Patent: May 18, 1999

[54] INTERBODY FUSION DEVICE HAVING PARTIAL CIRCULAR SECTION CROSS-SECTIONAL SEGMENTS

[75] Inventors: Joseph P. Errico, Far Hills; Thomas J. Errico, Summit; James D. Ralph, Oakland, all of N.J.

[73] Assignee: TechSys Medical, LLC, Summit, N.J.

[21] Appl. No.: 08/899,851

[22] Filed: Jul. 24, 1997

[51] Int. Cl.[6] ................................................ A61F 2/44
[52] U.S. Cl. ............................................................ 623/17
[58] Field of Search .................... 623/16, 17; 606/61, 606/60

[56] References Cited

U.S. PATENT DOCUMENTS

| | | | |
|---|---|---|---|
| 2,677,369 | 5/1954 | Knowles | 623/17 X |
| 4,863,477 | 9/1989 | Monson | 623/17 |
| 5,425,772 | 6/1995 | Brantigan | 623/17 |
| 5,443,514 | 8/1995 | Steffer | 623/17 |
| 5,522,899 | 6/1996 | Michelson | 606/61 X |
| 5,607,424 | 3/1997 | Tropiano | 606/61 |
| 5,658,335 | 8/1997 | Allen | 623/17 |
| 5,658,337 | 8/1997 | Kohrs et al. | 623/17 |
| 5,702,450 | 12/1997 | Bisserie | 623/17 |

FOREIGN PATENT DOCUMENTS

| | | | |
|---|---|---|---|
| 405208029 | 8/1993 | Japan | 623/17 |
| 1107854 | 8/1984 | U.S.S.R. | 623/17 |

*Primary Examiner*—Mary Beth Jones
*Attorney, Agent, or Firm*—Joseph P. Errico, Esq.

[57] ABSTRACT

A tubular interbody fusion device having flat upper and lower surfaces including multiple parallel ratcheted blade ridges having opposing orientations, concave exterior side walls, an interior axial bore having inwardly directed ratcheted ridges, and a plurality of through holes extending from the upper and lower surfaces into the interior bore, from the sides into the interior bore, and from the upper and lower surfaces through the side walls.

16 Claims, 5 Drawing Sheets

INTERBODY FUSION DEVICE HAVING PARTIAL CIRCULAR SECTION CROSS-SECTIONAL SEGMENTS

BACKGROUND OF THE INVENTION

1. Field of the Invention

This invention relates generally to a spinal implant assembly for implantation into the intervertebral space between adjacent vertebral bones to potentiate fusion, and more particularly to an implantable device having superior lateral stability and overall strength.

2. Description of the Prior Art

The bones and connective tissue of an adult human spinal column consists of more than 20 discrete bones coupled sequentially to one another by a tri-joint complex which consists of an anterior disc and the two posterior facet joints, the anterior discs of adjacent bones being cushioned by cartilage spacers referred to as intervertebral discs. These more than 20 bones are anatomically categorized as being members of one of four classifications: cervical, thoracic, lumbar, or sacral. The cervical portion of the spine, which comprises the top of the spine, up to the base of the skull, includes the first 7 vertebrae. The intermediate 12 bones are the thoracic vertebrae, and connect to the lower spine comprising the 5 lumbar vertebrae. The base of the spine is the sacral bones (including the coccyx). The component bones of the cervical spine are generally smaller than those of the thoracic spine, which are in turn smaller than those of the lumbar region. The sacral region connects laterally to the pelvis. While the sacral region is an integral part of the spine, for the purposes of fusion surgeries and for this disclosure, the word spine shall refer only to the cervical, thoracic, and lumbar regions.

The spinal column of bones is highly complex in that it includes over twenty bones coupled to one another, housing and protecting critical elements of the nervous system having innumerable peripheral nerves and circulatory bodies in close proximity. In spite of these complications, the spine is a highly flexible structure, capable of a high degree of curvature and twist in nearly every direction.

Genetic or developmental irregularities, trauma, chronic stress, tumors, and degenerative wear are a few of the causes which can result in spinal pathologies for which surgical intervention may be necessary. A variety of systems have been disclosed in the art which achieve immobilization and/or fusion of adjacent bones by implanting artificial assemblies in or on the spinal column. The region of the back which needs to be immobilized, as well as the individual variations in anatomy, determine the appropriate surgical protocol and implantation assembly. With respect to the failure of the intervertebral disc, the interbody fusion cage has generated substantial interest because it can be implanted laparoscopically into the anterior of the spine, thus reducing operating room time, patient recovery time, and scarification.

Referring now to FIGS. 1 and 2, in which a side perspective view of an intervertebral body cage and an anterior perspective view of a post implantation spinal column are shown, respectively, a more complete description of these devices of the prior art is herein provided. These cages 10 generally comprise tubular metal body 12 having an external surface threading 14. They are inserted transverse to the axis of the spine 16, into preformed cylindrical holes at the junction of adjacent vertebral bodies (in FIG. 2 the pair of cages 10 are inserted between the fifth lumbar vertebra (L5) and the top of the sacrum (S1). Two cages 10 are generally inserted side by side with the external threading 14 tapping into the lower surface of the vertebral bone above (L5), and the upper surface of the vertebral bone (S1) below. The cages 10 include holes 18 through which the adjacent bones are to grow. Additional material, for example autogenous bone graft materials, may be inserted into the hollow interior 20 of the cage 10 to incite or accelerate the growth of the bone into the cage. End caps (not shown) are often utilized to hold the bone graft material within the cage 10.

These cages of the prior art have enjoyed medical success in promoting fusion and grossly approximating proper disc height, however, they do have specific drawbacks which limit their effectiveness. First among these drawbacks is that the devices, once implanted, do not permit the spine to retain its original and proper curvature. Causing a fusion to grow and immobilize the spine at a curvature which is not natural can cause discomfort and potentially damaging effects.

A second concern with respect to cylindrical implants of this type is that there will be a tendency for the devices to roll and/or slide. Such undesirable motion by the implant can cause loosening, or worse, complete dislocation from its proper position.

A third limitation of these devices is that the overall volume for true bone fusion growth is limited by the geometry of the tubular device, i.e., much of the fusion must grow through the tubular section itself. Much issue has been taken with the fact that dependence upon fusion growth within the device at a microscopic level is not sufficient to provide the true stability and immobilization necessary for total healing of the site.

It is, therefore, an object of the present invention to provide a new and novel vertebral/intervertebral spacer which conforms to the natural curvature of the patient's spine.

It is further an object of the present invention to minimize the risk of dislocation by providing a geometric shape which is more suitable for stable positioning than cylindrical implants.

It is further an object of the present invention to provide a device for implantation into the intervertebral space which provides greater volume external to the device for bone fusion growth.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is an interbody fusion implant device comprising an elongate structure having a central axial bore, concave side walls, and upper and lower surfaces which are flat. More particularly, with respect to the overall shape of the present invention, the exterior surfaces of the side walls of the device are concave, resembling arc sections of a tube which have been positioned such that the convex surfaces face inward toward one another. The interior surfaces of the side walls, however, are also concave insofar as they mutually form the axial bore. The upper and lower surfaces of the device are flat, connecting the side walls at the upper and lower portions thereof, respectively; the inner surfaces thereof completing the overall generally tubular shape of the axial bore. The upper and lower surfaces include a plurality of stabilization ridges which extend perpendicularly to the overall axis of the device. The upper and lower surfaces further include a plurality of through holes disposed between the stabilization ridges. A number of the through holes extend from points along the central axis of the flat exterior surface of the device (upper or lower surface) into the central axial bore. Other through holes extend from lateral positions on the flat exterior surfaces to holes in the concave exterior surface of the corresponding side wall.

In a preferred embodiment, the side walls of the device are tapered along the axial extent of the device such that the upper and lower surfaces are not parallel, and more particularly, have a convergence angle which permits proper lordosis to be maintained.

The ridges disposed on the upper and lower flat surfaces have an overall curvate shape insofar as they comprise circular arc sections; integral with the lateral edges of the upper or lower surface, and rising to a maximum at the central axial position above the flat surface. It is further preferable that the ridges be sharp, even serrated, thereby comprising a radial blade in cross-section, such that the ridges may firmly grip the bone against which the corresponding flat surface is placed. In addition, the cross-sectional shape of the ridges may further include a biased thickening at the joining with the flat surface insofar as one lateral surface of the ridge may be more gently sloped than the other. In a preferred embodiment, the ridges of one axial end have a biased thickening in one direction (for example having the gentle sloping lateral surface of the ridge facing toward the distal end of the device), while the ridges at the other axial end have their biased thickening in the opposite sense (in this example having the gentle sloping lateral surface of the ridge facing toward the proximal end). This opposing sense imparts greater holding strength to the device as compared with threaded, smooth, or even uniformly ridged devices insofar as the ridges collectively form a barrier to movement in either direction.

The interior of the device, which is the axial bore, is preferably also contoured with at least one conformation which provides additional strength and/or bone graft retention. In a first embodiment, the interior surface of the bore includes a disc-shaped plate positioned at a midpoint along the axis of the device and aligned perpendicularly to the axis of the bore, with the edges of the disc integrally formed with the interior surfaces of the device and otherwise occluding the bore. This interior plate is provided as a substantial reinforcement of the overall structure. The disc-plate may include at least one small through hole extending through the middle thereof in order to permit allograft bone material to communicate through the entire axial extent of the device.

In alternative embodiments, the interior surface of the bore may include a plurality of small inwardly directed flanges. These flanges may be designed with a similar collective thickness biasing in order to enhance the retention of allograft materials. In the preferred embodiment of this design, the flanges are continuous hoops integrally formed with the interior surface of the bore, therein providing enhanced structural strength to the overall device as well as the enhanced allograft retention.

In perferred embodiments, the side walls also include a plurality of through holes (in addition to the ones which communicate directly with the through holes formed at the lateral positions of the upper and lower surfaces, as set forth more fully above) formed therein for direct bone growth communication with the interior of the axial bore. It shall be understood that the particular shape of the holes, i.e., circular, elliptical, polygonal, etc., is of little consequence with respect to the overall functionality of the implant, provided only that the through holes be large enough to permit bone matrix growth therethrough, and are not so large as to detrimentally weaken the overall structural integrity of the device.

During the implantation procedure, the surgeon first removes the degenerated disc material from between the vertebral bodies and then prepares the adjacent exposed bone surfaces for the introduction of an implant of the present invention (in the present explanation, a pair of devices are to be positioned in the intervertebral space). The device is introduced into the intervertebral space initially with the concave side walls facing the opposing exposed faces of the adjacent bones. The width of the device is preferably less than its height such that by subsequent rotation of the device by 90 degrees about its elongate axis the ridges of the upper and lower flat surfaces cut into the exposed faces of the adjacent bones, therein securely fixing itself into the space. In a dual device procedure, the first device is positioned in the intervertebral space at a laterally offset position. A second device is then similarly implanted at the opposite laterally offset position. The space between the devices, i.e., between the opposing concave side walls of the adjacent devices, should be ideally suited for additional allograft material, which is in communication with the exposed bone faces directly and through the lateral through holes of the upper and lower flat faces of the devices.

In each of the embodiments which include a lordotic convergence angle of the upper and lower flat surfaces, it is anticipated that, in most procedures, the devices will be inserted with the narrower distal ends disposed in the same direction. It is, however, anticipated that conformational irregularities, such as scoliosis and other congenital defects may necessitate the use of dual devices which are otherwise directed, or in which one device includes a lordotic angulation and the other does not.

DETAILED DESCRIPTION OF THE PREFERRED EMBODIMENT

Figure 1:
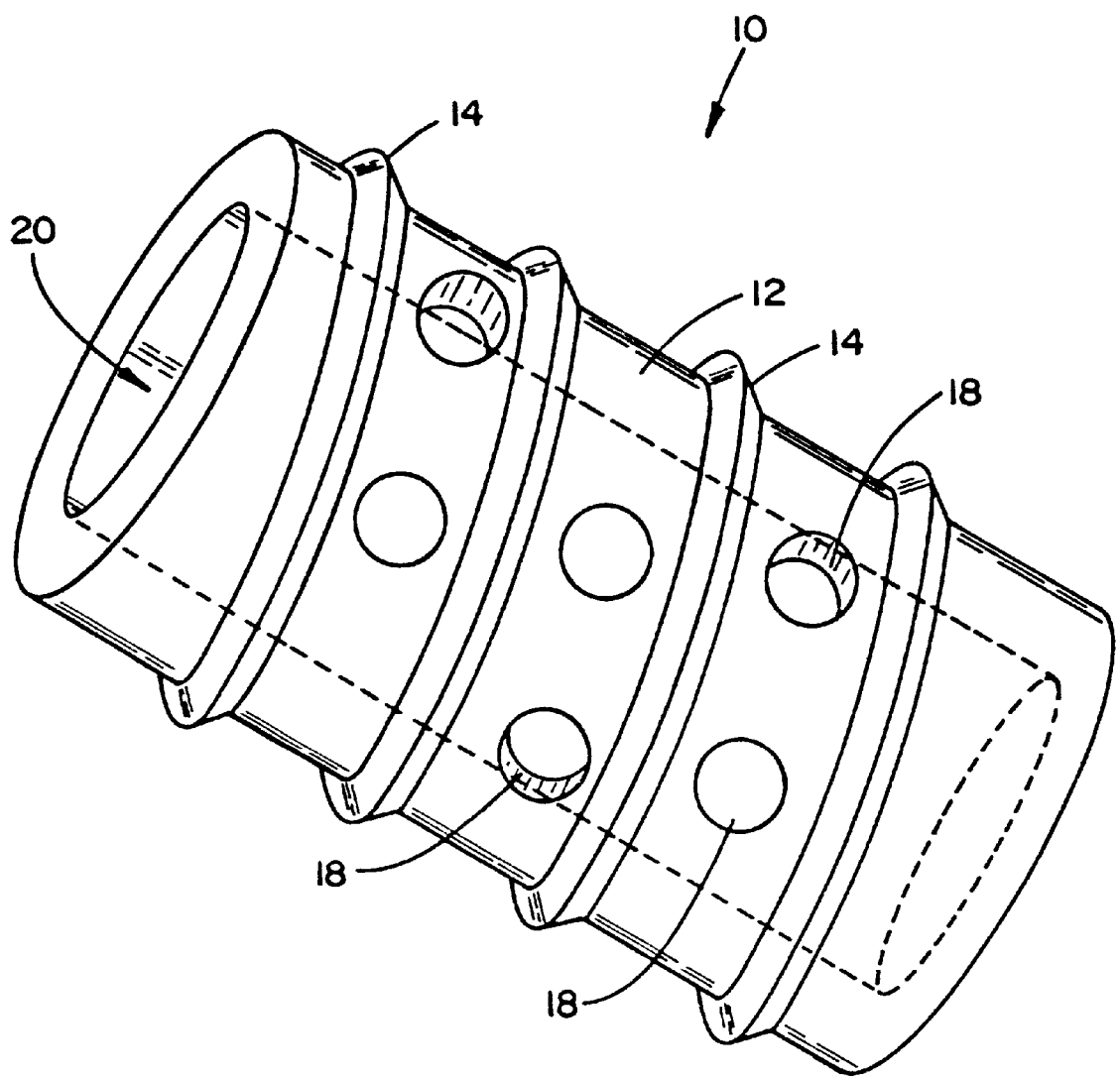
FIG. 1 is a side perspective view of an interbody fusion device of the prior art.
Figure 2:
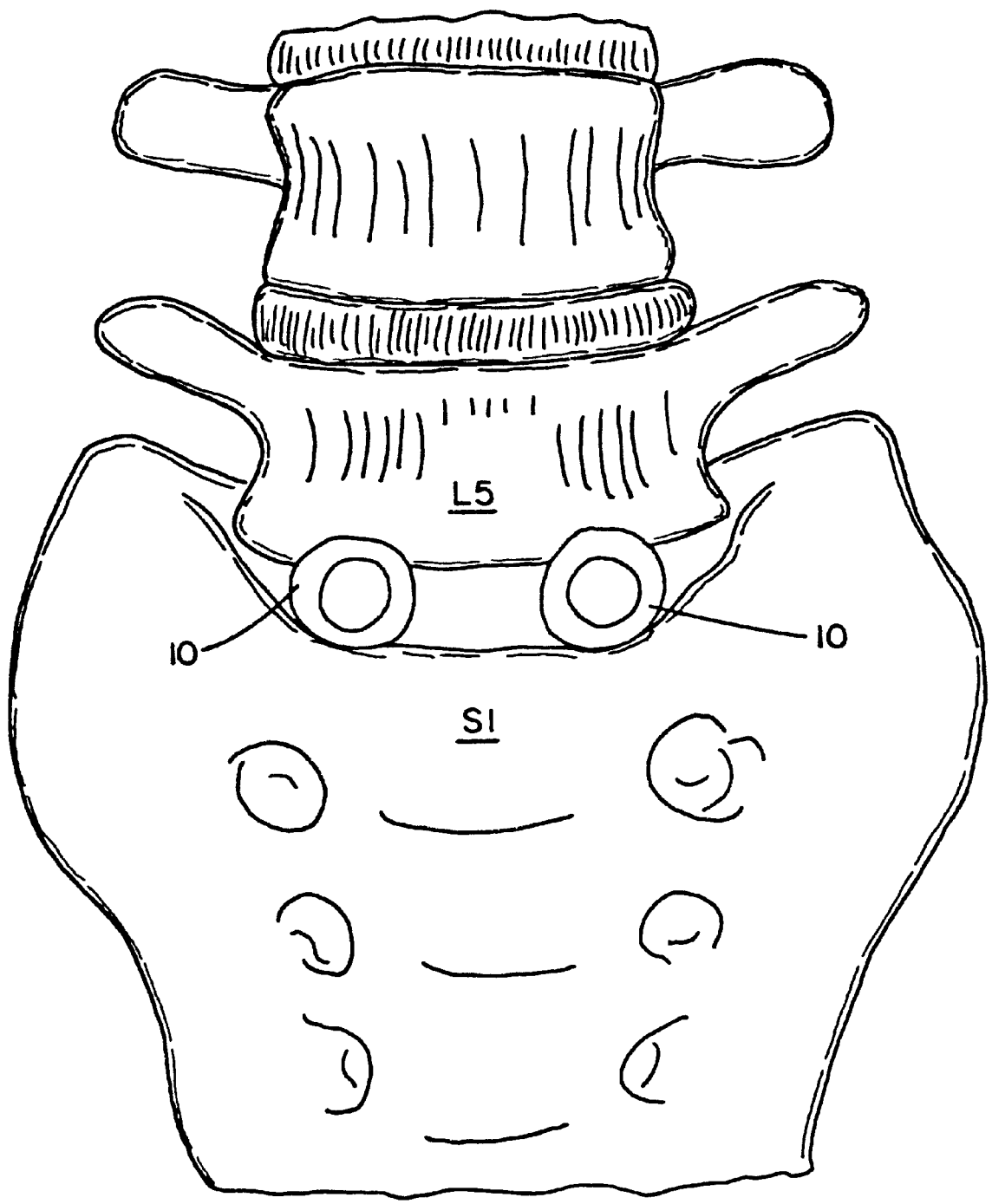
FIG. 2 is a front view of the anterior portion of the lumbo-sacral region of a human spine, into which a pair of interbody fusion devices of the type shown in FIG. 1 have been implanted.
Figure 3:
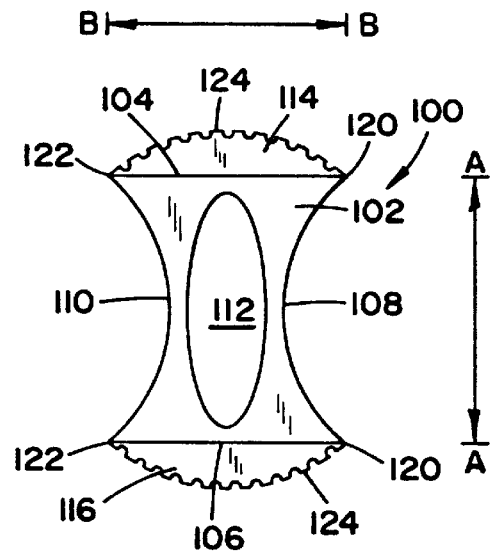
FIG. 3 is an end view of a one embodiment of the present invention.

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope. Like numbers refer to similar features of like elements throughout.

Referring now to FIGS. 3–6 end, top, side and side cross-section views of a first embodiment of the present invention are shown. More particularly, with respect to FIG. 3, the first embodiment 100 of the present invention comprises a tubular shaped body 102 having parallel upper and lower flat external surfaces 104,106, respectively, concave exterior side walls 108,110 and a central bore 112. In addition, the upper and lower flat external surfaces 104,106 each include ridges 114 and 116 which extend outwardly from the surfaces 104,106, respectively, perpendicular to the surfaces and to the overall axis of the body (i.e., the axis of the bore 112). The overall height of the device, as measured along a line A—A extending from the upper external flat surface 104 to the lower flat surface 106 and is perpendicular to both surfaces and the overall axis of the body, is greater than the maximum width of the device as measured along a line B—B extending between the lateral edges 120,122 of either the upper or lower flat external surfaces 104,106 at the points where the side walls 108,110 meet the upper or lower surfaces, and extending perpendicular to the axis of the bore 112 and parallel to the flat upper and lower surfaces 104,106.

More particularly, with respect to the ridges 114,116, it is preferable that the ridges be curvate, as arc sections, rising from the lateral edges 120,122 of the upper or lower surfaces to a maximum height above (or below) the midpoint of the corresponding surface 104,106. It is further desirable that the ridges form blades, which may, most preferably have a serration 124. This serrated blade is ideally suited for cutting through bone, and is therefore ideally suited for positioning of the device as shall be more fully set forth hereinbelow with respect to procedural use.

Figure 4:
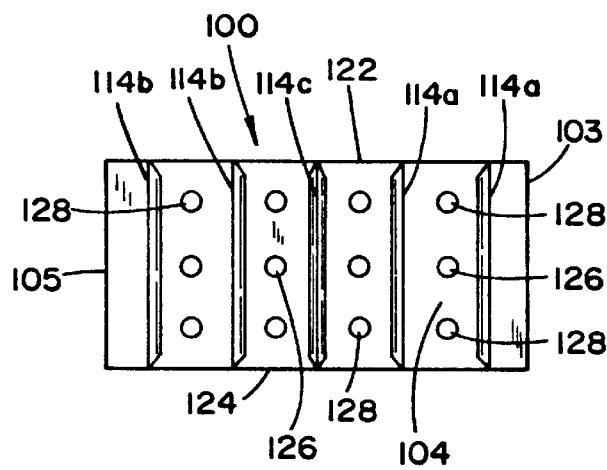
FIG. 4 is a top view of the embodiment of the present invention illustrated in FIG. 3.
Figure 5:
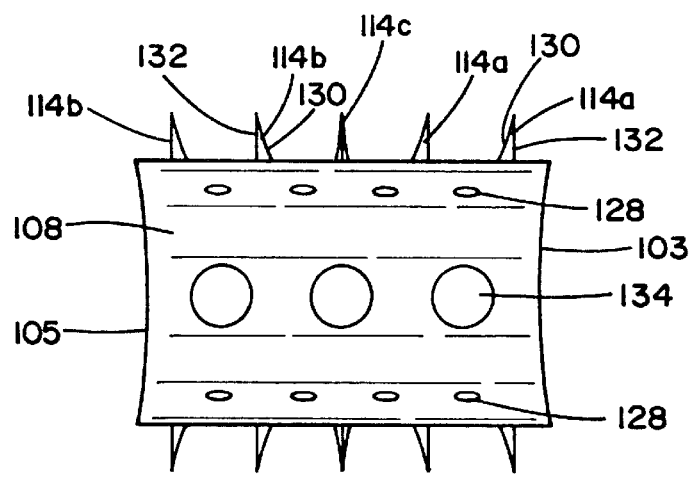
FIG. 5 is a side perspective view of the embodiment of the present invention illustrated in FIGS. 3 and 4.

Referring now also to FIGS. 4 and 5, top and side perspective views of the first embodiment 100 of the present invention is further provided. The ridges 114 of the upper (and lower) external surfaces 104 (and 106) are divided into three types. The first type 114a are provided on one side (nearest to proximal end 103, shown in FIGS. 4 and 5 on the right side) and have an eccentric bias to their overall form such that the inner surface 130 is sloped more gently as compared with the outer surface, thus making the ridge 114a into a ratchet having a proximal orientation. The second type of ridge 114b is provided on the other end of the device (nearest the distal end 105, shown in FIGS. 4 and 5 on the left side) and, again has the inner lateral surface 130 more gently sloped than the outer lateral surface 132, therein making the ridge 114b a ratchet having a distal orientation. The third type of ridge 114c, disposed at the center of the surface 104 (or 106) has a symmetrical lateral conformation and does not act as a ratchet. The opposing ratcheting of the device permits greater stability once it has been implanted as it resists pullout or migration in both directions.

The upper and lower flat external surfaces 104 and 106, as well as the concave side walls 108 and 110 further include a series of through holes 126,128, 134 which communicate with one another and with the axial bore 112, therein permitting bony ingrowth into and through the implant device (and into the bone graft material which is disposed within the axial bore 112). The through holes are divided into three types; the first type 126 being disposed on the upper and lower surfaces 104,106, generally along the axial midpoints of their respective surfaces, and between the ridges 114a–c. These first type through holes 126 extend from the external surface into the axial bore 112. The second type of through hole 128 are disposed at lateral positions on the upper and lower surfaces 104,106 of the device 100, and communicating through to the upper (or lower) surfaces of the concave side walls 108,110. The third type of through hole 134 extends from points along the axial midline of the side walls 108,110 and extends into the axial bore 112.

Figure 6:
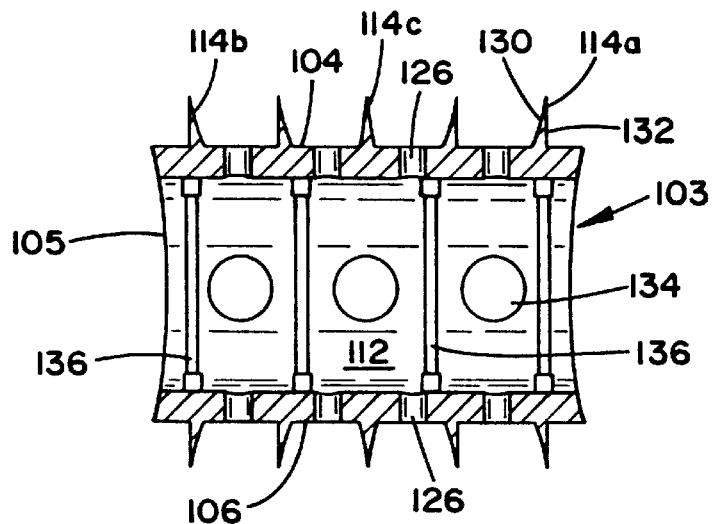
FIG. 6 is a side cross-sectional view of the embodiment of the present invention illustrated in FIGS. 3–5.

Referring now to FIG. 6, the interior conformation of the axial bore 112 is provided in a side cross-section view. The interior conformation of the axial bore 112 includes a plurality of inwardly directed protuberances 136, herein shown as circumferential ridges having alternating ratcheted shapes. These interior ridges 136 are provided for two purposes; the first being an increased structureal strength associated with the additional hoop support provided by the thickened sections, and the second being an increased holding stability for bone graft material disposed in the axial bore 112.

Figure 7:
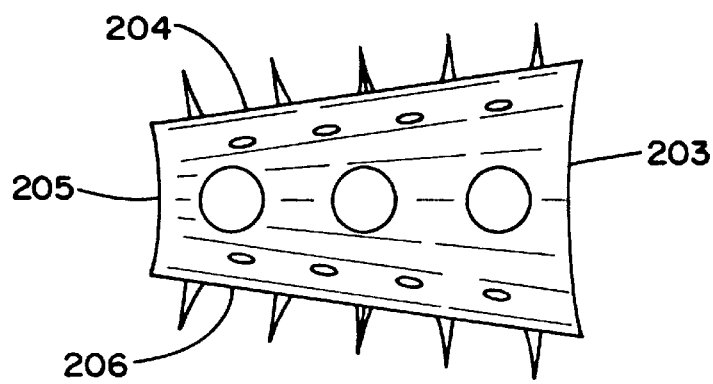
FIG. 7 is a side perspective view of an alternative embodiment of the present invention.
Figure 8:
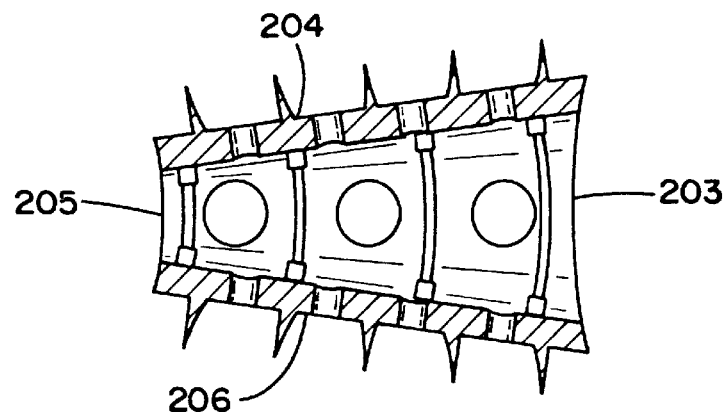
FIG. 8 is a side cross-sectional view of the alternative embodiment illustrated in FIG. 7.
Figure 9:
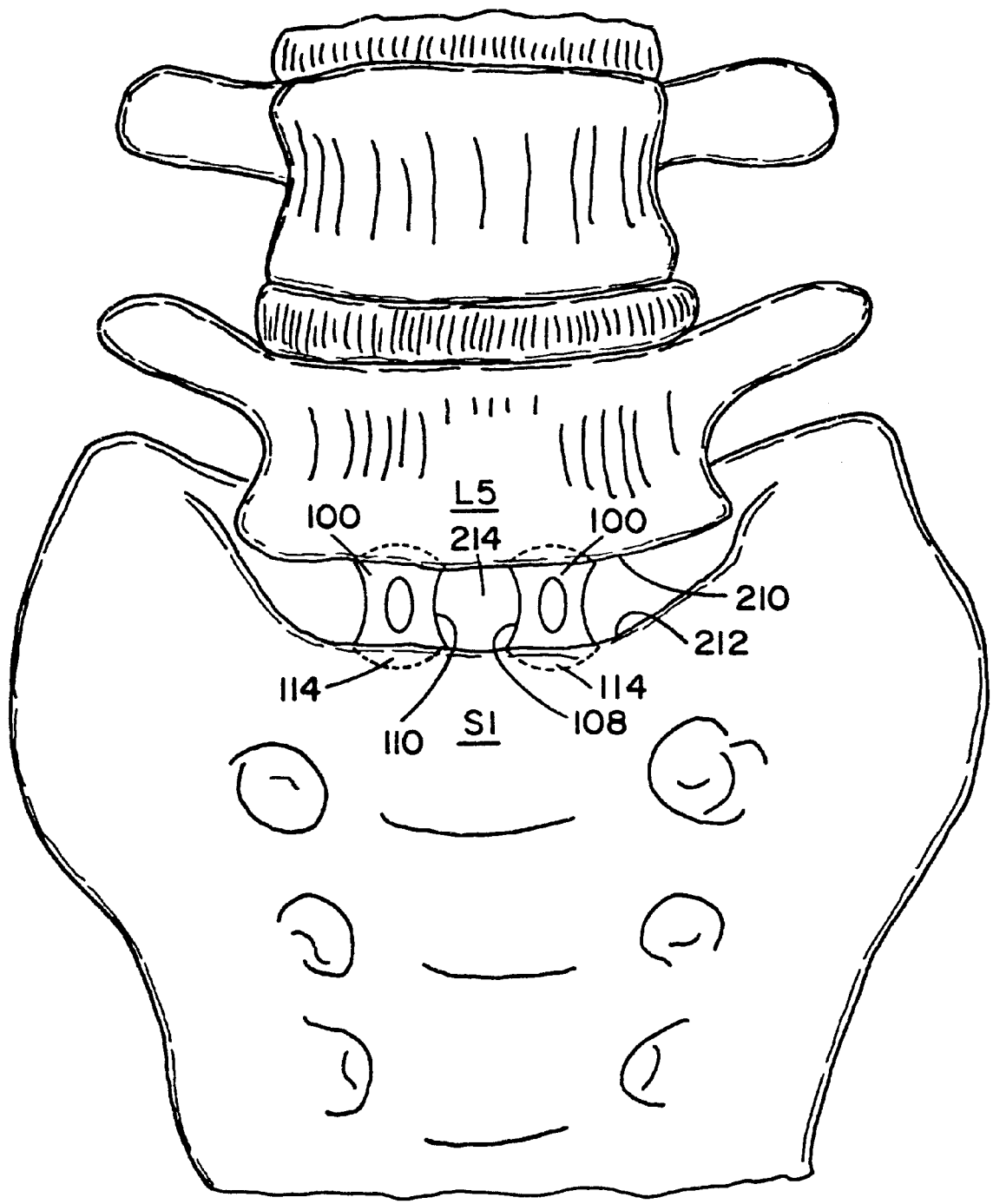
FIG. 9 is a front view of the anterior portion of the lumbo-sacral region of a human spine, into which a pair of interbody fusion implant devices of the present invention, as illustrated in FIGS. 3–6, has been implanted.

Referring now to FIGS. 7 and 8, a second embodiment 200 of the present invention is shown in side perspective and side cross-section views, respectively. In this second embodiment, the upper and lower flat external surfaces 204,206 are not parallel as they were in the first embodiment 100, but rather form a convergent taper, rendering the device narrower at the distal end 205 and wider at the proximal end 203. With respect to all other features, however, i.e., the concave side walls the through holes, the interior and exterior ridges, etc., the second embodiment 200 is similar to the first 100. This tapered embodiment is provided so that the device can provide lordotic support for the adjacent vertebrae, therein providing proper anotomical contouring of the spine.

During the implantation procedure of either embodiment, the surgeon first removes the degenerated disc material from between the vertebral bodies L5 and S1 and prepares the adjacent exposed bone surfaces 210, 212 for the introduction of a first implant 100 (or 200) of the present invention (in the present explanation, a pair of devices are to be positioned in the intervertebral space). The device 100 is introduced into the intervertebral space initially with the concave side walls 108,110 facing the opposing exposed faces 210,212, respectively, of the adjacent bones L5 and S1, respectively. As the width of the device is preferably less than its height, subsequent rotation of the device by 90 degrees about its elongate axis the ridges 114 of the upper and lower flat 104,106 surfaces cut into the exposed faces 210,212 of the adjacent bones, therein securely fixing itself into the space. In a dual device procedure, the first device is positioned in the intervertebral space at a laterally offset position. A second device is then similarly implanted at the opposite laterally offset position. The space 214 between the devices, i.e., between the opposing concave side walls 108,110 of the adjacent devices is ideally suited for additional bone graft material, insofar as it is in direct communication with the exposed bone faces 210,212 and through the lateral through holes 134 of each device, and through the lateral through holes 128 of the upper and lower flat faces of each device.

While there has been described and illustrated implantation devices for stabilizing and immobilizing regions of the spine by inserting a shape conforming cage in the intervertebral space between adjacent vertebral bodies, it will be apparent to those skilled in the art that variations and modifications are possible without deviating from the broad spirit and principle of the present invention which shall be limited solely by the scope of the claims appended hereto.

We claim:

1. An interbody fusion implant, said implant comprising a tubular shaped body having flat upper and lower exterior surfaces and exterior side walls which are concave.

2. The interbody fusion implant device set forth in claim 1, further comprising at least one through hole formed therein, which through hole extends from an exterior surface to an interior of said tubular shaped body.

3. The interbody fusion implant device as set forth in claim 1, further comprising at least one through hole extending from one of said flat exterior surfaces to one of said concave exterior side walls.

4. The interbody fusion implant device as set forth in claim 1, further comprising at least one inwardly directed protuberance formed on an inner surface of said tubular shaped body.

5. The interbody fusion implant device as set forth in claim 4, wherein said at least one inwardly directed protuberance comprises at least two inwardly directed protuberances formed on the inner surface of said tubular shaped boy, wherein at least one of said protuberances forms a ratchet oriented toward a proximal end of said tubular body, and at least one other protuberance forms a ratchet oriented toward a distal end of said tubular body.

6. The interbody fusion implant device as set forth in claim 1, further comprising at least one ridge formed on at least one of said upper and lower flat exterior surfaces.

7. The interbody fusion implant device as set forth in claim 6, wherein said at least one ridge extends out from said corresponding flat exterior surface perpendicular to the axis of the tubular body.

8. The interbody fusion implant device as set forth in claim 7, wherein said at least one ridge has a curvate outer edge.

9. The interbody fusion implant device as set forth in claim 7, wherein said at least one ridge has a serrated outer edge.

10. The interbody fusion implant device as set forth in claim 1, further comprising a plurality of ridges formed on each of said upper and lower flat exterior surfaces, said plurality of ridges on each flat surface being aligned perpendicular to the elongate axis of the device, and said ridges being spaced apart from one another of said corresponding surface.

11. The interbody fusion implant device as set forth in claim 10, wherein there are at least two of said ridges on each of the upper and lower surfaces and at least one of said ridges on at least one of said upper and lower surfaces comprises a ratchet oriented toward a proximal end of said tubular body, and at least one other of said ridges on said at least one of said upper and lower surfaces comprises a ratchet oriented toward a distal end of said tubular body.

12. The interbody fusion implant device as set forth in claim 1, wherein said flat upper and lower exterior surfaces form mutually parallel planes.

13. The interbody fusion implant device as set forth in claim 1, wherein said flat upper and lower exterior surfaces are convergently angled such that the device is tapered along its elongate axis.

14. The interbody fusion implant device as set forth in claim 1, further comprising at least one inwardly directed flange formed on an inner surface of said tubular shaped body and extending fully around the interior perimeter of said tubular body.

15. The interbody fusion implant device as set forth in claim 1, wherein the height of the device as measured along a line perpendicular to both the axis of the tubular body and the planes of the upper and lower flat exterior surfaces is greater than the greatest width of the device as measured along a line perpendicular to the axis of the tubular body and parallel to the planes of the upper and lower flat exterior surfaces.

16. A hollow tubular interbody fusion implant, comprising:

flat upper and lower external surfaces;

side walls having inwardly bowed exterior surfaces defining a concave cross-sectional external shaped;

a plurality of through holes formed therein, a first set of said through holes being formed in said upper and lower external surfaces and extending through to said interior of said tubular body, a second set of said through holes being formed in said side walls and extending through to said interior of said tubular body, and a third set of said through holes being formed in said upper and lower external surfaces and extending through to said inwardly bowed exterior surfaces of said said walls;

a plurality of ridges formed on each of the upper and lower flat external surfaces, said ridges being disposed pendendicular to the axis of the tubular body; and a plurality of ridges formed on an interior surface of said tubular body.

* * * * *